United States Patent

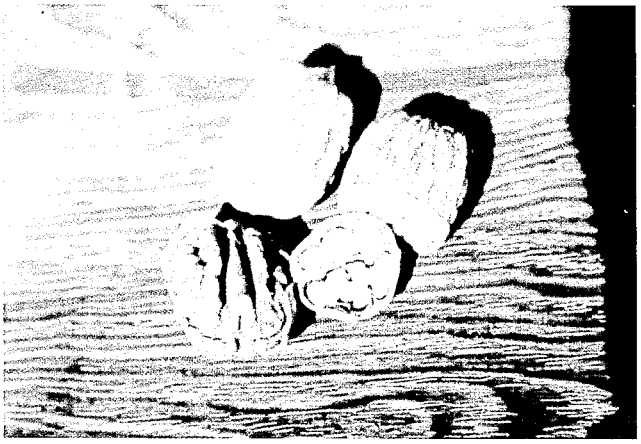
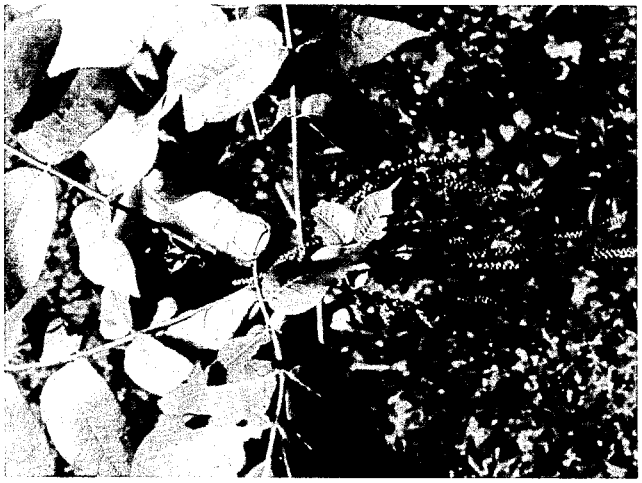
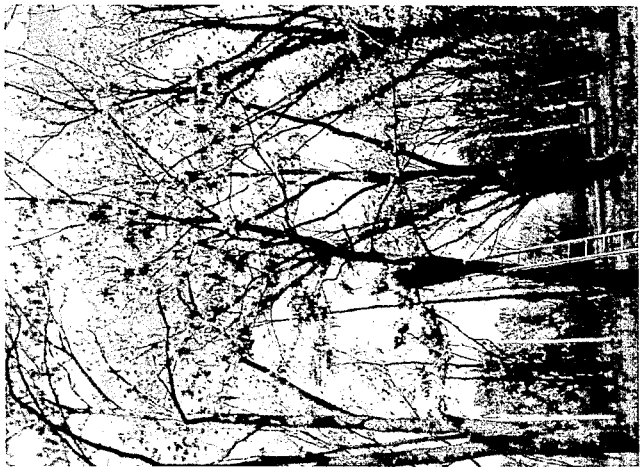

Plant Pat. 3,877

Patented May 4, 1976

3,877

HICAN TREE

George James, Brunswick, Mo., assignor to James Pecan Farms, Inc., Brunswick, Mo.

Filed Apr. 8, 1975, Ser. No. 566,070

Int. Cl. A01h *5/03*

U.S. Cl. Plt.—30 1 Claim

The present invention relates to a new and distinct variety of hican tree which was discovered by me as a seedling of unknown parentage growing on my cultivated property in Chariton County, near Brunswick, Mo.

For many years, I have been commercially growing on my property aforesaid nut trees of various kinds, and especially pecans, walnuts and hickories, some of which were originated and developed by me as seedlings derived from seed nuts which were planted by me, and others derived from selections of naturally occurring seedlings. The present seedling, which is the subject hereof, came to my attention during the course of the cultivation and care of my nut tree farms aforesaid. While working one day near a corner of one of my farms, my attention was attracted to a particular tree which appeared to be different from any others which I was then growing. The bark on the trunk of that tree resembled typical pecan tree bark, while the branches and foliage resembled typical hickories. Even more significantly, the tree bore a heavy crop of nuts of exceptionally large size (much larger than those of northern pecans), and which were shaped like pecan nuts, but were rougher in appearance and resembled the appearance of hickory nuts. I concluded from the foregoing that the new seedling apparently was the result of a natural cross of a northern seedling pecan of unknown parentage with a shellbark hickory of unknown parentage. I therefore cleared the area of brush, weed trees and other vegetation around the new seedling, and carefully preserved the seedling for further observations.

In due course, I also asexually reproduced the new seedling by both grafting and budding, as performed by me on my aforementioned farms. Continued observations and tests of the original seedling, as well as its progeny derived therefrom as aforesaid, have confirmed that its distinctive features as initially recognized by me come true, among others subsequently observed, and I am convinced that the new seedling represents a new, distinct and commercially valuable variety of hican tree, as principally evidenced by the following unique combination of characteristics which are outstanding therein:

(1) Bark on the tree trunk which is typical of pecan tree bark;
(2) Branches and foliage which are typical of those of hickories;
(3) A relatively heavy nut bearing habit, with the nuts being borne in clustres of usually 3 to 5 nuts per cluster;
(4) A nut shape generally similar to that of pecan nuts, but the nuts being much larger than the nuts of northern pecans and having rough and much thinner shells which resemble hickory nuts, with the nut shells being heavier than those of pecans and the nuts averaging 42 in number per pound;
(5) A high cracking percentage averaging 52%, with the ability of being cracked readily by regular conventional pecan cracking machinery, and the kernels being plump and solid and releasing easily and mostly in halves;
(6) An excellent kernel flavor which is distinctly similar to the typical flavor of hickories;
(7) The production of attractive catkins which range between 8 and 12 inches in length but which are smaller in diameter than those of either pecans or hickories, and the catkins being light green in color;

(8) An early nut maturity usually occurring about September first in Missouri, which enables extension of the commercial growing of the nuts to states both east and north of Missouri and to any other places where hickory nuts are now grown; and
(9) Excellent hardiness and self-fertility.

The accompanying drawing shows a typical tree of my new hican variety, as well as typical mature nut specimens, with some of the mature nut specimens being depicted in cross-section, and also shows a typical twig specimen with foliage and catkins, and a young nut cluster in the early stage of its growth, as illustrated in color.

The following is a detailed description of my new hican variety, with color terminology in accordance with the Nickerson Color Fan, published by Munsell Color Company, Inc., of Baltimore, Md., except where general color terms of ordinary dictionary significance are obvious:

LOCALITY WHERE GROWN AND OBSERVED: Chariton County, Missouri.

PARENTAGE: Natural seedling of unknown parentage.

PROPAGATION: Holds its distinguishing characteristics through succeeding propagations by both budding and grafting.

DATES OF FIRST AND LAST PICKINGS: About September 1 and September 10, respectively.

MATURITY SEASON: About 4 months or 120 days.

TREE: Self-fertile.
- Size—Small.
- Productivity—Good; regular bearer.
- Growth habit—Vigorous; very hardy. Limbs—Medium heaviness; smooth, resemble hickory limbs.
- Wood—Rough; trunk resembles pecan tree trunk.
- Foliage—Average abundance.
  - Size—Leaflets average about 5 inches long and about 3 inches wide.
  - Color—Light green, usually ranging between near Strong Yellow Green, hue, 2.5 GY7/10 and near Moderate Yellow Green, hue 2.5 GY5/5.
- Buds—
  - Shape—Long; very sharp-pointed.
  - Color—Light green.

NUTS:
- Ripening—Even.
- Time of harvesting—From about September 5 to about September 15.
- Quantity—Heavy (equal to or better than hickories, and heavier than any hican I have ever observed).
- Maturity—Before frost in Missouri area; usually early September.
- Tenacity—Free.
- Cluster—Large; average of 3 nuts per cluster but sometimes 5 and occasionally 2.
- Size—
  - Length—About 1⅞ inches.
  - Diameter—About 1⅛ inches.
  - Shell thickness—About 1/16 inch.
- Weight—Average 42 nuts per pound.
- Shape—More like pecan than hickory.
  - Base—Blunt.
  - Point—Carries width well to the point.
- Shell—Slightly heavier than shell of nuts of northern pecan seedlings, but very thin in comparison with shellbark hickory nuts; cracks and releases very easily, and can be readily cracked by regular pecan cracking machinery; high cracking ratio averaging 52%.
- Color—Light brown, ranging from near Strong Orange Yellow, hue, 7.5 YR7/11 to near Dark Orange Yellow, hue, 7.5 YR6/9 with darker streaks near Strong Brown, hue, 2.5 YR4/7 and some black blotches on apex end.

Kernel—Plump.

Shape—Similar to shellbark hickory kernels.

Texture—Solid.

Flavor—Pronounced hickory flavor.

Sutures—Open on one half and slightly closed on other half.

Color—Light brown on outer surface and creamy white inside.

I claim:

1. A new and distinct variety of hican tree, substantially as herein shown and described, characterized particularly as to novelty by the unique combination of bark on the tree trunk which is typical of pecan tree bark; branches and foliage which are typical of those of hickories; a self-fertile and relatively heavy nut bearing habit, with the nuts being borne in clusters of usually 3 to 5 nuts per cluster; a nut shape generally similar to that of pecan nuts, but the nuts being much larger than the nuts of northern pecans and having rough and much thinner shells which resemble hickory nuts, with the nut shells being heavier than those of pecans, and the nuts averaging 42 in number per pound; a high cracking percentage of 52%, with the ability of being cracked readily by regular conventional pecan cracking machinery, and the kernels being plump and solid and releasing easily and mostly in halves; an excellent kernel flavor which is distinctly similar to the typical flavor of hickories; the production of attractive catkins which range between 8 and 12 inches in length but which are smaller in diameter than those of either pecans or hickories, and the catkins being light green in color; an early nut maturity usually occurring about September first in Missouri, which enables extension of the commercial growing of the nuts to states both east and north of Missouri and to ayn other places where hickory nuts are now grown; and excellent hardiness.

No references cited.

ROBERT E. BAGWILL, Primary Examiner